US00PP16514P2

(12) United States Plant Patent
Trees

(10) Patent No.: US PP16,514 P2
(45) Date of Patent: May 9, 2006

(54) ***GERANIUM* PLANT NAMED 'BALFANIMCAR'**

(50) Latin Name: *Pelargonium×hortorum*
Varietal Denomination: Balfanimcar

(75) Inventor: Scott C. Trees, Shell Beach, CA (US)

(73) Assignee: Ball Horticultural Company, West Chicago, IL (US)

( * ) Notice: Subject to any disclaimer, the term of this patent is extended or adjusted under 35 U.S.C. 154(b) by 117 days.

(21) Appl. No.: 11/016,488

(22) Filed: Dec. 17, 2004

(51) Int. Cl.
*A01H 5/00* (2006.01)

(52) U.S. Cl. ..... Plt./330
(58) Field of Classification Search ..... Plt./330
See application file for complete search history.

*Primary Examiner*—Kent Bell
(74) *Attorney, Agent, or Firm*—Wood, Phillips, Katz, Clark & Mortimer

(57) ABSTRACT

A new and distinct cultivar of *Geranium* plant named 'Balfanimcar' characterized by its semi-double red-colored flowers, dark green-colored foliage with zonation, and vigorous, upright and mounded growth habit.

1 Drawing Sheet

Latin name of genus and species of plant claimed: *Pelargonium×hortorum.*
Variety denomination: 'Balfanimcar'.

BACKGROUND OF THE INVENTION

The present invention relates to a new and distinct cultivar of *Geranium* plant botanically known as *Pelargonium× hortorum* and hereinafter referred to by the cultivar name 'Balfanimcar'.

The new cultivar originated in a controlled breeding program in Arroyo Grande, Calif., during August 2000. The objective of the breeding program was the development of *Geranium* cultivars with a vigorous, upright mounded growth habit, dark green-colored foliage, and new and unique flower color.

The female (seed) parent of the new cultivar was the proprietary *Pelargonium×hortorum* breeding line 'BFP-2341', not patented, characterized by its semi-double scarlet-colored flowers and dark green-colored foliage with a distinct zone. The male (pollen) parent of the new cultivar was 'Americana Dark Red', U.S. Plant Pat. No. 9,307, characterized by its semi-double dark red-colored flowers and medium green-colored foliage. The new *Geranium* was discovered and selected by the inventor as a single flowering plant within the progeny of the above stated cross-pollination during May 2002 at Arroyo Grande, Calif.

Asexual reproduction of the new cultivar by terminal stem cuttings since May 2002 at Arroyo Grande, Calif. and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfanimcar' as a new and distinct cultivar of *Geranium* plant.

1. Semi-double red-colored flowers.
2. Dark green-colored foliage with zonation.
3. Vigorous, upright and mounded growth habit.

Plants of the new cultivar differ from plants of the female primarily in plant vigor and foliage color and from plants of the male parent primarily in flower color.

Of the many commercially available *Geranium* cultivars known to the inventor, the most similar in comparison to the new cultivar is 'Americana Dark Red', U.S. Plant Pat. No. 9,307. However, in side by side comparisons, plants of the new cultivar differed from plants of 'Americana Dark Red' in the following characteristics:

1. Plants of the new cultivar exhibit lighter, brighter flower color than plants of 'Americana Dark Red'.
2. Plants of the new cultivar exhibit a darker green leaf color than plants of 'Americana Dark Red'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Balfanimcar'. The plants were grown for 8 weeks in a greenhouse at West Chicago, Ill.

DETAILED BOTANICAL DESCRIPTION

Figure 1:
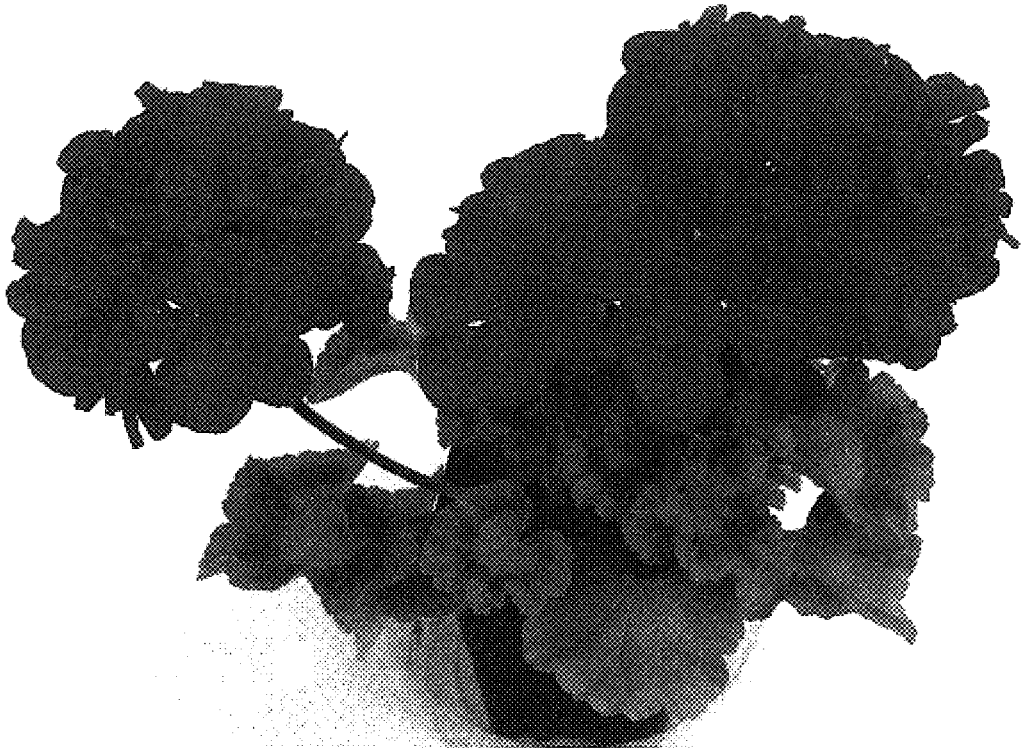
FIG. 1 illustrates a side view of the overall growth and flowering habit of 'Balfanimcar'.
Figure 2:
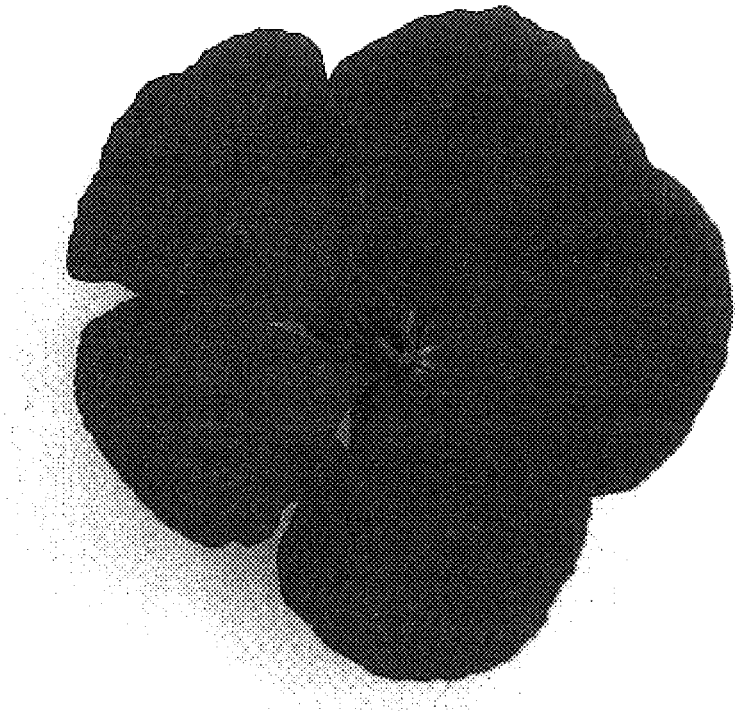
FIG. 2 illustrates a close-up view of a single flower of 'Balfanimcar'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2001 edition, except where general color terms of ordinary significance are used. The color values were determined on Jul. 30, 2004 between 10:00 and 11:45 a.m. under natural light conditions in West Chicago, Ill.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks utilizing a soilless growth medium. Greenhouse temperatures were maintained at approximately 65°–70° F. (18°–21° C.) during the day and approximately 60°–65° F. (15°–18° C.) during the night. Greenhouse light levels of 4,000–6,000 footcandles were maintained during the day. Plants were pinched at three weeks after the planting of a rooted cutting.

Botanical classification: *Pelargonium×hortorum* cultivar Balfanimcar.

Parentage:

*Female parent.*—Proprietary selection 'BFP-2341', not patented.

*Male parent.*—'Americana Dark Red', U.S. Plant Pat. No. 9,307.

Propagation:

*Type cutting.*—Terminal stem.

*Time to initiate roots.*—Approximately 10 to 14 days.

*Time to produce a rooted cutting.*—Approximately 21 to 28 days.

*Root description.*—Fibrous.

*Rooting habit.*—Freely branching.

Plant description:

*Crop time.*—Approximately 8–9 weeks from rooted cutting.

*Growth habit and general appearance.*—Vigorous, upright and mounded.

*Size.*—Height from soil level to top of plant plane: Approximately 20.3 cm. Width/area of spread: Approximately 28.1 cm.

*Branching habit.*—Freely basal branching. Approximately 3 branches per plant.

*Branch description.*—Length: Approximately 5.1 cm. Diameter: Approximately 8.1 mm. Texture: Velutinous. Color: 144A. Internode length at center of branch: Approximately 6.8 mm.

*Foliage description.*—Number of leaves per lateral branch: Approximately 12. Form: Simple. Fragrance: None. Arrangement: Opposite. Shape: Reniform. Margin: Crenate. Apex: Rounded. Base: Cordate, open. Venation pattern: Palmate. Upper surface texture: Velutinous. Lower surface texture: Velutinous with denser pubescence along veins. Size: Mature leaf length: Approximately 4.5 cm. Mature leaf width: Approximately 7.3 cm. Color of mature foliage: Upper surface: 137A with veins of 144A and zone of 137A at the inner ½. Color of mature foliage: Lower surface: Darker than 147A with veins of 144A. Petiole length: Approximately 6.3 cm. Petiole diameter: Approximately 2.3 mm. Petiole Texture: Velutinous on both upper and lower surface. Petiole color: 146B.

Flowering description:

*Outdoor flowering habit.*—'Balfanimcar' is freely flowering under outdoor growing conditions with substantially continuous blooming from spring through autumn and year round in greenhouse environment.

*Time to first flower.*—Approximately 8 weeks after planting of rooted cutting.

*Lastingness of individual bloom.*—Approximately 5–7 days.

Inflorescence description:

*Type.*—Hemispherical umbel. Position: Above foliage. Number of open umbels at any one time: 4. Number of developing umbels at any one time: 2. Umbel diameter: Approximately 8.4 cm. Umbel height/depth: Approximately 5.8 cm. Number of flowers per umbel: Approximately 11.

*Peduncle.*—Strong, erect. Length: Approximately 11.5 cm. Diameter: Approximately 3.5 mm. Texture: Glandular pubescent. Gland color: Colorless, transluscent. Color: 143D.

Flower description:

*Bud rate of opening.*—Generally takes approximately 3–5 days for buds to progress from first color to fully open flower.

*Bud just before opening.*—Shape: Round. Length: Approximately 1 cm. Diameter: Approximately 7 mm. Petal color: 46C. Sepal color: 143C.

*Corolla.*—Form: Semi-double. Shape: Round, slightly cupped. Diameter/Width: Approximately 4.7 cm. Depth: Approximately 1.7 cm. Fragrance: None. Persistent.

*Petals/petaloids.*—Quantity: Approximately 7 petals and 7 petaloids, of varying shape, per flower. Arrangement: Imbricate. Shape: Obovate. Apex: Obtuse. Base: Attenuate. Margin: Entire. Texture of upper and lower surface: Glabrous. Upper petal/petaloid length: Approximately 2.5 cm. Upper petal/petaloid width: Approximately 1.6 cm. Lower petal/petaloid length: Approximately 2.2 cm. Lower petal/petaloid width: Approximately 1.7 cm. Color of upper petals/petaloids: Fully opened, upper surface: Lighter and brighter than 45B with 44B and venation of 46A at base. Lower surface: 44B with venation of 46A. Color of lower petals/petaloids: Fully open upper surface: Lighter and brighter than 45B with venation of 46C. Fully open lower surface: About 44B with venation of about 46A.

*Pedicel.*—Strength: Strong. Angle: Acute. Length: Approximately 2.7 cm. Diameter: Approximately 1.1 mm. Texture: Glandular pubescent. Gland color: Transluscent. Color: 144B with overlay of 185A.

*Calyx/sepals.*—Quantity per flower: 5. Shape: Lanceolate. Tip: Acuminate. Base: Truncate. Margin: Entire. Sepal length: Approximately 1.2 cm. Sepal width: 3.3 mm. Texture of both upper/inside surface and lower/outside surface: Moderately glandular. Color of upper and lower surface: N144A at apex/distil, 185A at base/proximal.

*Reproductive organs.*—Androecium: Stamen number: 9 per flower. Filament length: Approximately 6 mm. Filament color: N155B. Anther shape: Oval. Anther quantity: Approximately 9. Anther length: Approximately 2 mm. Mature anther color: 186A. Pollen amount: Abundant. Pollen color 168A. Gynoecium: Pistil quantity: One per flower. Pistil length: Approximately 8.9 mm. Stigma shape: 5 pointed star. Stigma length: 1.5 mm. Stigma color: 187C. Style length: 2.8 mm. Style color: 187D. Ovary length: 4.6 mm. Ovary diameter: 2 mm. Ovary texture: Sericeous. Ovary color: 143A.

Seed and fruit production: Neither seed nor fruit production has been observed.

Disease and pest resistance: Resistance to pathogens and pests common to *geraniums* has not been observed.

What is claimed is:

1. A new and distinct cultivar of *Geranium* plant named 'Balfanimcar', substantially as herein shown and described.

* * * * *